United States Patent [19]

Weiss

[11] Patent Number: 4,520,810
[45] Date of Patent: Jun. 4, 1985

[54] APPARATUS FOR PERFORMING AN EMERGENCY CRICOTHYROTOMY

[76] Inventor: Sol Weiss, 17227 Quesan Pl., Encino, Calif. 91316

[21] Appl. No.: 603,369

[22] Filed: Apr. 24, 1984

Related U.S. Application Data

[63] Continuation of Ser. No. 307,764, Oct. 2, 1981, abandoned.

[51] Int. Cl.³ .................. A61B 17/32; A61M 16/00
[52] U.S. Cl. ........................ 128/200.26; 128/305.3
[58] Field of Search ............. 128/207.15, 200.26, 128/DIG. 26, 305.3; 604/158-163, 165

[56] References Cited

U.S. PATENT DOCUMENTS

| | | | |
|---|---|---|---|
| 2,623,520 | 12/1952 | Bamford et al. | 604/165 |
| 2,820,457 | 1/1958 | Phillips | 128/200.26 |
| 3,817,250 | 6/1974 | Weiss et al. | 128/305 |
| 3,916,903 | 11/1975 | Pozzi | 128/305.3 |
| 4,170,232 | 10/1979 | Khoury | 128/DIG. 26 X |

Primary Examiner—Michael H. Thaler
Attorney, Agent, or Firm—Gerald L. Price

[57] ABSTRACT

An improved apparatus and method for performing an emergency cricothyrotomy comprising a tracheostomy device which can be inserted into a patient's neck without danger of puncture of the posterior wall and which permits insertion of an airway tube without popping out of the device from the incision in the patient's neck or penetrating the posterior wall. An airway tube can be quickly and easily substituted for another airway tube of differing internal diameter without the need for redefining the puncture area or utilization of additional instrumentation. If desired, a closed system can be quickly and easily coupled to the device without the need for making a bigger opening in the patient's neck.

1 Claim, 16 Drawing Figures

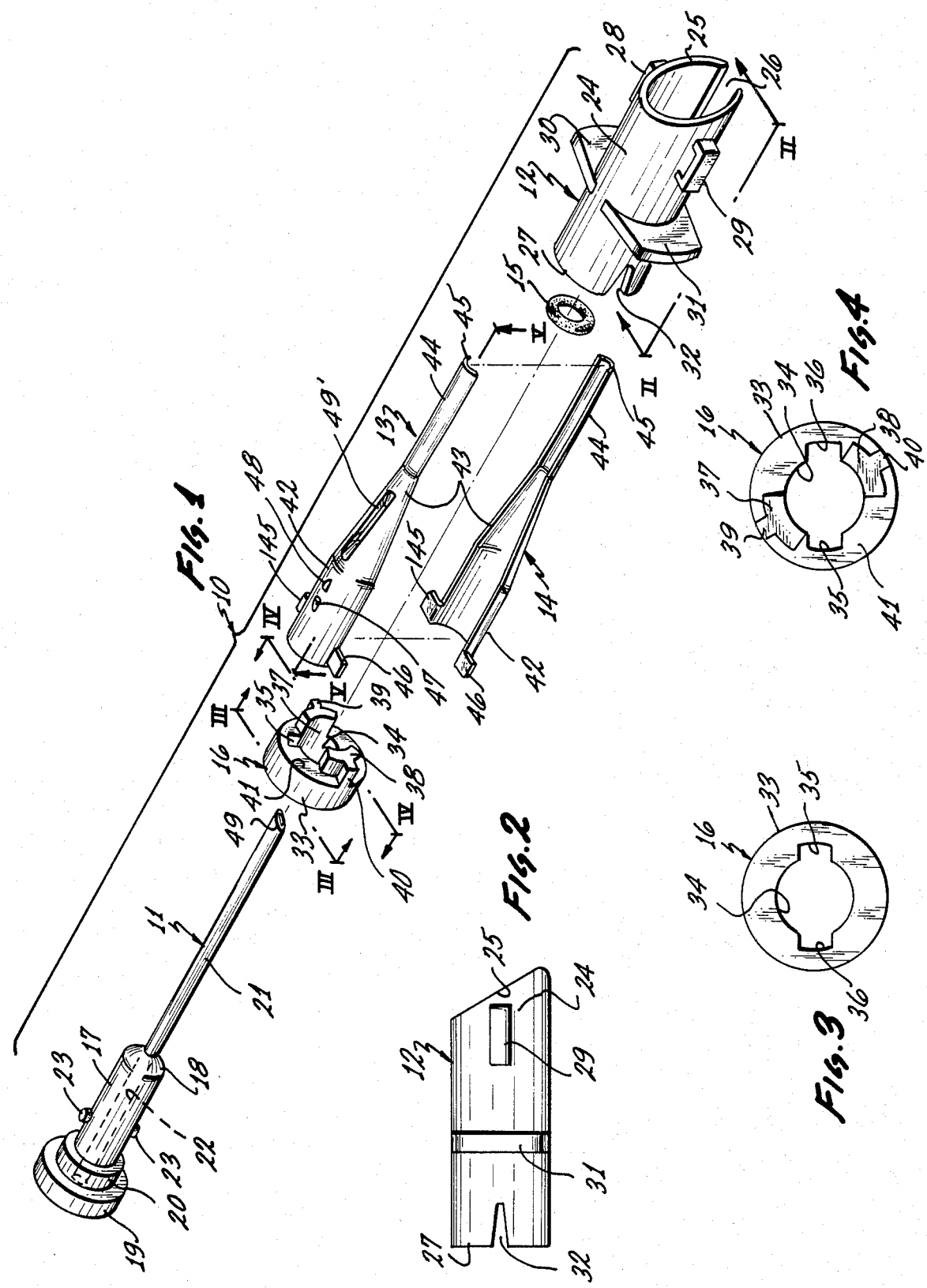

APPARATUS FOR PERFORMING AN EMERGENCY CRICOTHYROTOMY

This is a continuation of application Ser. No. 307,764, filed Oct. 2, 1981, now abandoned.

BACKGROUND OF THE INVENTION

1. Field of the Invention

The invention relates to tracheostomy devices and, more particularly, to improved apparatus for performing an emergency cricothyrotomy.

2. Description of the Prior Art

Tracheostomy is an operation for the purpose of relieving an obstruction of the respiratory passage. One such prior art device is described in detail in U.S. Pat. No. 3,688,773 of which I am the inventor. In U.S. Pat. No. 3,817,250, of which I am co-inventor, an improvement on the device of my earlier patent is described. In general, both these prior art devices comprise an expandable needle, enlarged in a rear section and tapering to a sharp point for puncturing the skin and tissue of a patient. The sharp end of the needle is used to make the puncture and the entire needle is inserted into the trachea. An air tube is then inserted into the needle, expanding the same, and into the tracheal area to allow the patient to breathe.

Although these prior art devices are a substantial improvement over the devices heretofore known, there is a danger that the sharp ends of the needle could be inserted too far into the trachea puncturing the soft posterior wall causing the death of the patient. Further, insertion of the air tube into the expandable needle separated the needle halves by engagement of one end of the air tube with a reduced inner wall portion of the needle. This engagement, if not carried out carefully and properly, could kick the device out of the tracheal incision or separate the sharp needle ends in the tracheal passage again possibly puncturing the posterior wall and killing the patient.

There is thus a need for improving such devices so that an emergency cricothyrotomy may be performed with little danger of puncture of the posterior wall even if the operator is relatively unskilled.

SUMMARY OF THE INVENTION

It is an object of the invention to provide an improved tracheostomy device which can be used to relieve an obstruction of the respiratory passage of a patient with little danger of puncture of the posterior wall of the trachea or popping out of the device.

It is still another object of this invention to provide an improved method for performing an emergency cricothyrotomy which can be quickly and easily carried out by an operator with little danger of puncture of the posterior wall of the trachea of the patient.

It is a further object of this invention to provide an improved tracheostomy device and method which permits substitution of one size external air passage for another without need for additional incision or other instrumentation.

It is another object of this invention to provide an improved method for performing an emergency cricothyrotomy wherein a closed system may be coupled to a tracheostomy device without the need for enlarging the incision in the patient's neck.

These and other objects are preferably accomplished by providing a tracheostomy device which can be inserted into a patient's neck without danger of puncture of the posterior wall and which permits insertion of an airway tube without popping out of the device from the incision in the patient's neck or penetrating the posterior wall. An airway tube of one internal diameter can be quickly and easily substituted for an airway tube of differing diameter without the need for redefining the puncture area or utilization of additional instrumentation. If desired, a closed system can be quickly and easily coupled to the device without the need for making a bigger opening in the patient's neck.

BRIEF DESCRIPTION OF THE DRAWING

FIG. 1 is an exploded view of a portion of the improved apparatus of the invention;

FIG. 2 is a view taken along lines II—II of FIG. 1;

FIG. 3 is a view taken along lines III—III of FIG. 1;

FIG. 4 is a view taken along lines IV—IV of FIG. 1;

DESCRIPTION OF THE PREFERRED EMBODIMENT

Figure 5:
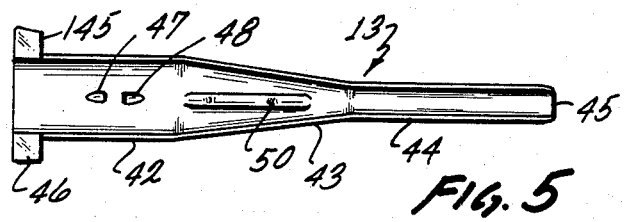
FIG. 5 is a view taken along lines V—V of FIG. 1.

Referring now to FIG. 1 of the drawing, apparatus 10 is shown in exploded view and comprises a stylet 11, a housing section 12, a pair of mating needle sections 13, 14 adapted to be inserted into housing section 12 and a resilient O-ring 15 for retaining the needle sections internally of housing section 12 as will be discussed. An end cap 16 is provided for closing off the open end of housing section 12 after insertion of needle sections 13,14.

Stylet 11 is comprised of a main body portion 17 which may have a smooth or rounded end 18 at one end and an enlarged cap or head portion 19 at the other end. A reduced section head portion 20 may be provided between head portion 19 and body portion 17. An elongated hollow tubular section 21 extends from body portion 17, the interior thereof communicating with an air passageway 22 through body portion 17. A pair of spaced indexing means, such as lugs or ears 23 are provided on the exterior of body portion 17 again for reasons to be discussed further hereinbelow. The components of stylet 11 may be molded from plastic or other similar material except for section 21 which may be of metal or the like insertible into body portion 17.

Referring now to the housing section 12 and particularly to both FIGS. 1 and 2, section 12 includes a generally hollow tubular main body portion 24 terminating in a distal end 25 at an angle with respect to the central longitudinal axis of the body portion 24, e.g., an angle of about 30 degrees. A generally rectangular cut-out section 26 is provided in distal end 25 along the outer wall of body portion 24 extending from the furthermost end of body portion 24 toward forward end 27.

A pair of spaced U-shaped brackets 28,29 are provided on the outer wall of body portion 24 as well as a pair of aligned elongated flanges 30,31 (or a single flange extending about body portion 24) on both sides of body portion 24. The entire housing section 12 and its various components may be of a single piece of plastic or the like. A pair of generally V-shaped cut-outs 32 (only one visible in FIG. 2) may be provided at forward end 27 for reasons to be discussed.

End cap 16 is shown in FIG. 1 and in detail in FIGS. 3 and 4. End cap 16 may also be of molded plastic and includes a generally circular main body portion 33 having a central aperture or passageway 34 (FIGS. 3 and 4) with a pair of internal keyways 35,36. A pair of arcuate protrusions 37,38, having outer ears 39,40, respectively, are provided on the distal end wall 41 of cap 16. Ears 39,40 are of a width related to the outermost width of cut-outs 32 in housing section 12 as will be discussed.

The needle sections 13,14 will now be discussed with reference to both FIGS. 1 and 5. It is to be understood that sections 13,14 are identical and reference to one will be applicable to the other.

Figure 6:
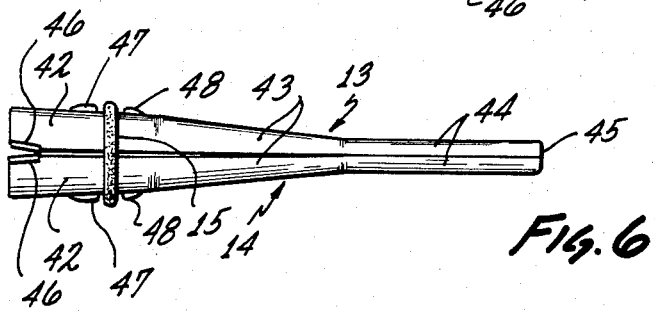
FIG. 6 is a vertical view showing part of the components of the apparatus of FIG. 1 in assembled position.

Thus, each needle section 13,14 includes a generally semi-circular main body portion 42 integral with a tapered portion 43 which is in turn integral with an elongated generally semi-circular needle end 44. As particularly contemplated in the present invention, the distal end 145 of needle section 13 is blunt, for reasons to be discussed, and the forward end of body portion 42 may include a pair of ears or flanges 145,46. A pair of spaced raised portions or protrusions 47,48 are formed on the outer wall of each needle section 13,14 (see particularly FIG. 1). As particularly contemplated in the present invention, an elongated groove 49' (FIG. 1) is formed in the outer wall of tapered portion 43 (protruding inwardly) thus forming an internal raised section 50 (see FIG. 5). All of the components of each needle section 13,14 may be comprised of a unitary piece of plastic, metal or other suitable material. Further, as discussed, each needle section 13,14 is identical so that the sections 13,14 can be placed together engaging at flanges 145,46 to form a unitary needle, as shown in FIG. 6, retained together by O-ring 15 encircling each section 13,14 and retained in predetermined position between the respective protrusions 47,48. Of course, any suitable resilient means may be used in place of O-ring 15, such as rubber, plastics, springs, etc. The position of protrusions 47,48 is predetermined to provide a desired hinge location for separation of the ends 44 of each needle section 13,14 as will be discussed.

The assembly of the described components is as follows. Needle sections 13,14 are joined via ring 15 as described with respect to FIG. 6. Ends 44 are inserted into housing section 12 until ends 44 protrude out of distal end 25 as should be obvious from FIG. 7. Flanges 145,46 enter cut-outs 32 and are retained therein. End cap 16 is then inserted into forward end 27 of housing section 12 with ears 39,40 entering V-shaped cut-outs 32 until distal end 41 abuts against the forward end wall 27 and ears 39,40 abut against flanges 145,46. Ears 39,40 may also be tapered to wedge into cut-outs 32 and protrusions 37,38 also abut against flanges 145,46 keeping needle sections 13,14 securely wedged in position. In practice, cap 16 may be welded or glued to housing section 12 after placement of needle sections 13,14.

Figure 7:
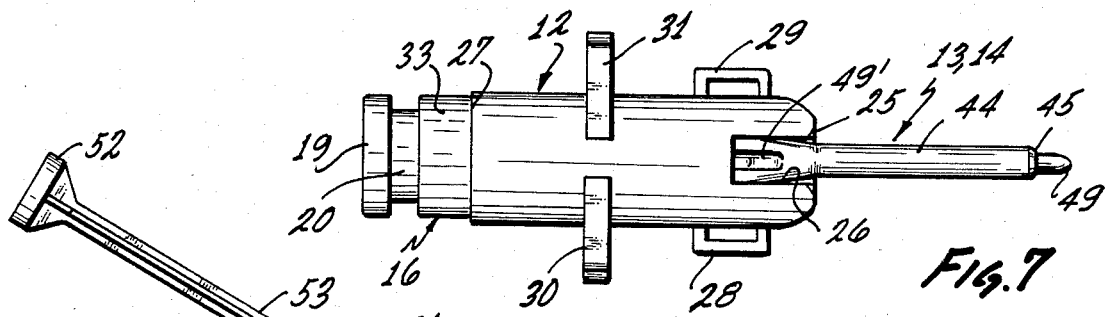
FIG. 7 is an assembled view of the apparatus of FIG. 1.

The tubular section 21 of stylet 11 is now inserted into the passageway through end cap 16 with ears 23 keying stylet 11 in keyways 35,36 on end cap 16. The rounded end 18 on body portion 17 facilitates entry should any foreign matter be present internally of needle sections 13,14. As shown in FIG. 7, the terminal or distal sharp cutting end 49 of stylet 11 thus protrudes beyond the distal ends 44 of needle sections 13,14. It is also cut at an angle for easy penetration, Indicia may be provided on housing section 12 adjacent cut-out section 26 to indicate the TOP or proper orientation of the device of FIGS. 1 through 7.

Figure 8:
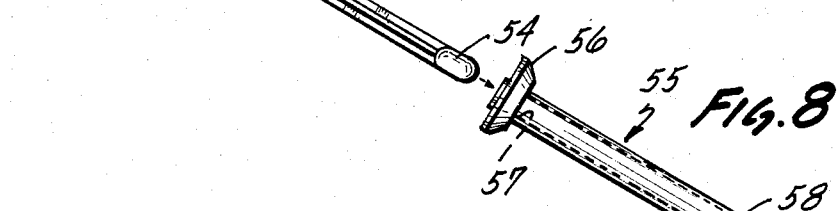
FIG. 8 is an exploded view of additional apparatus which, in conjunction with the apparatus of FIG. 1, comprises the improved apparatus of the invention.
Figure 9:
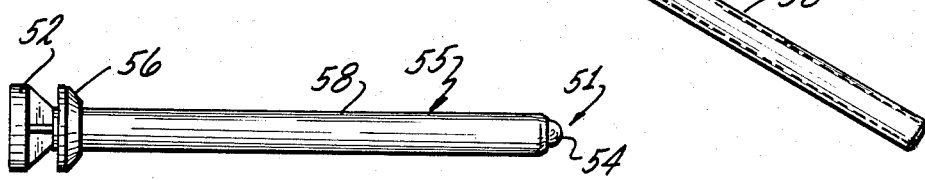
FIG. 9 is an assembled view of the apparatus of FIG. 8.

The improved method of using the device of FIGS. 1 to 7 will be discussed further hereinbelow. However, the device is intended to be used with air tubes of varying internal diameters. Thus, as shown in FIG. 8, a combined air tube 55 and obturator 51 is shown. Obturator 51 includes a cap 52 tapering to an elongated section 53 having a rounded distal end 54. Section 53 may be ribbed or X-shaped in cross-section. Obturator 51 may be of a unitary piece of suitable material, such as plastic. Air tube 55 includes a tapered end cap 56 which may include a central opening 57 receiving therein one end of an elongated hollow tube 58. Cap 56 may be of plastic or the like and tube 58 may be of any suitable material, such as stainless steel. Section 53 is adapted to be inserted through opening 57, as shown in FIG. 9, and the assembly shown in FIG. 9 is adapted to be inserted into housing section 12 when stylet 11 is removed therefrom, as will be discussed.

Various combinations of air tubes and obturators may be provided having various thicknesses and diameters so that the size of the air tube opening may be varied depending on the use of the device.

Figure 10:
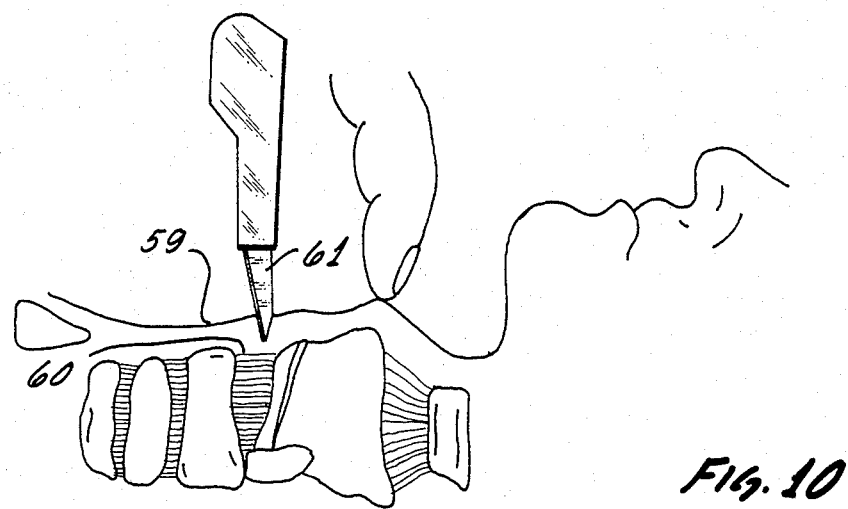
FIG. 10 through FIG. 13 and FIG. 15 illustrate the sequential steps in the improved method of my invention using the apparatus of FIGS. 1 through 9.

The operation of the device of FIGS. 1 through 9 will now be described with particular reference to FIGS. 10 through 15. As shown in FIG. 10, the neck 59 of the patient is hyperextended, if possible, and the cricothyroid membrane 60 identified. A scalpel blade 61 or the like is then used to incise the skin to a desired depth, such as one to two centimeters.

Figure 11:
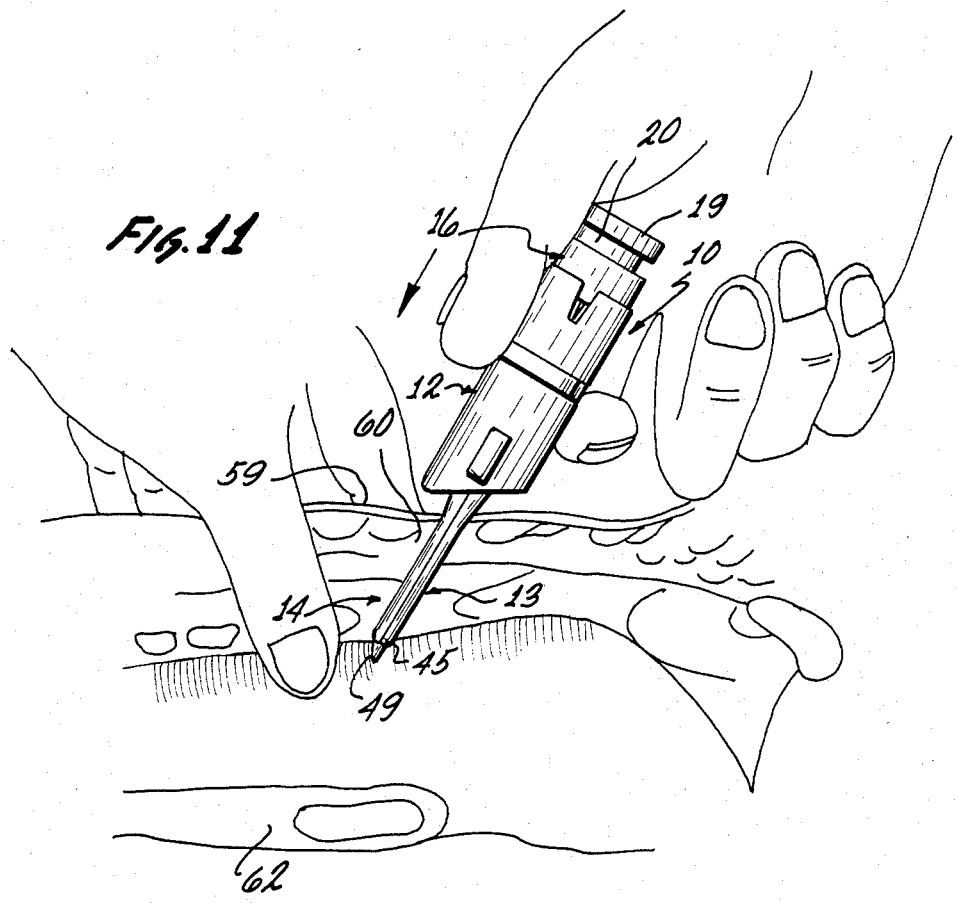
Figure 12:
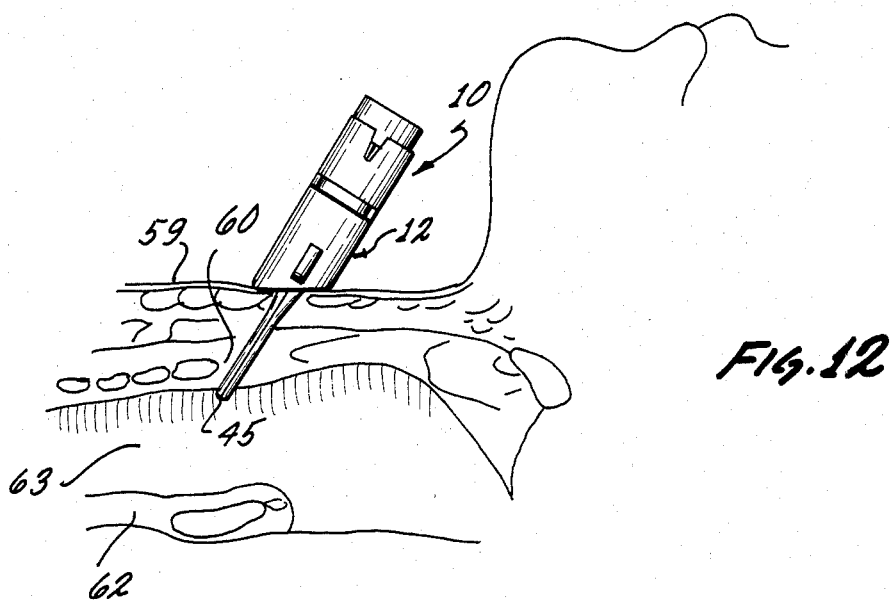

With the stylet 11 in position in housing section 12 as shown in FIG. 7, stylet end 49 and needle ends 44 are inserted through the incision in the skin as shown in FIG. 11. The apparatus 10 is inserted at an angle as shown (approximately the same angle as end 25 of housing section 12) until sharp end 49 cuts through the membrane 60. Thus, apparatus 10 is inserted until the operator feels a breaking through or popping of membrane 60 which is accompanied by a flush or expulsion of air through passageway 22. The angularity of apparatus 10 in FIG. 11 is such because the airway in the trachea 63 narrows and you don't want to overpenetrate. The stylet 11 is now removed by twisting out of housing section 12 and needle ends 44 are moved gently into the trachea 63 until end 25 rests on overlying skin 59. If the entire apparatus 10 can be freely rocked in position as shown in FIG. 12, this confirms to the operator that he is at the proper depth of penetration and not lodged on the posterior wall 62 of trachea 63. This is accomplished without danger of penetration of the posterior wall 62.

Figure 14:
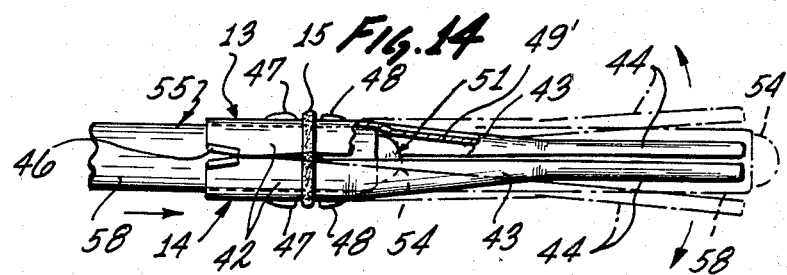
FIG. 14 is a detailed view of a portion of the apparatus of FIG. 13 illustrating the separating of the terminal ends of the needle segments.
Figure 13:
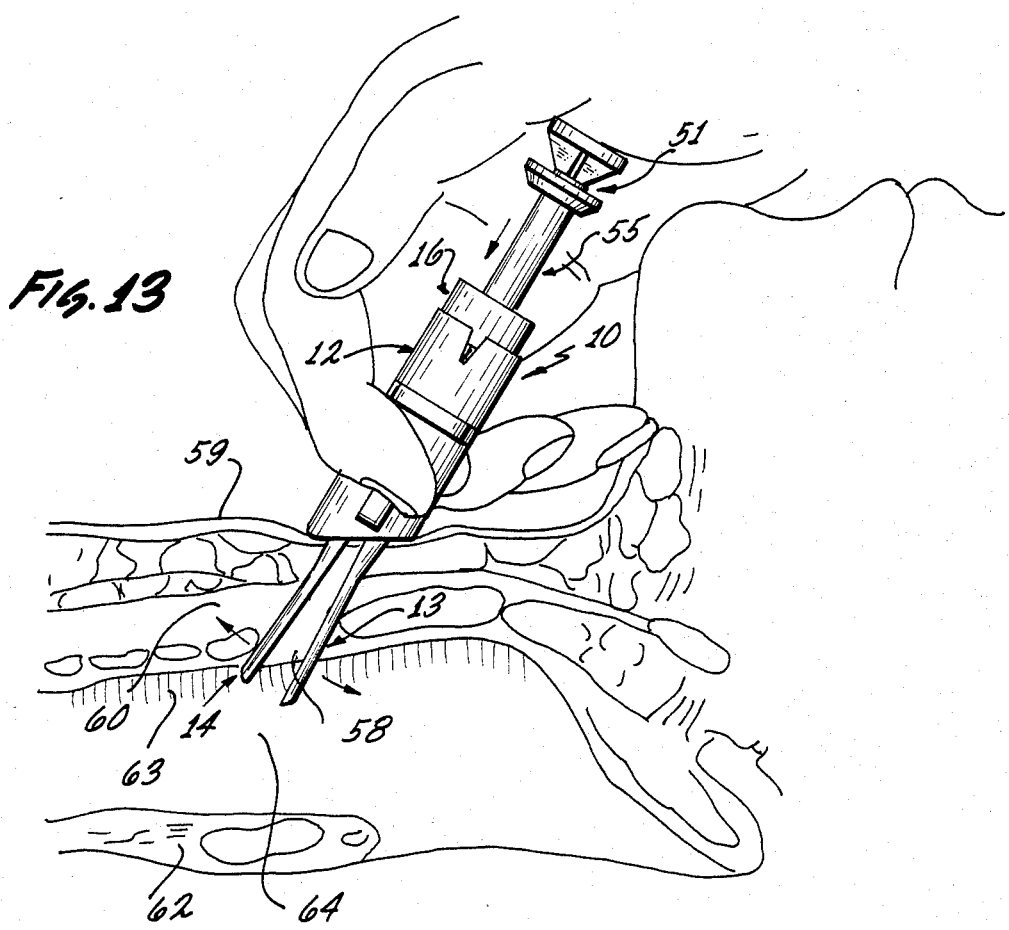

The operator may now select an air tube of a desired diameter and assemblies the same into a matching obturator. Thus, as shown in FIG. 13, obturator 51 is inserted into an air tube 55 and the middle and index fingers grasp housing section 12 below stabilizing flanges 30,31, with the thenar eminence pushing down on cap 52 thus pushing airway tube 55 and obturator 51 downward into the mating needle sections 13,14. These sections are of course divided lengthwise and spread apart under the resilience of O-ring 15, to accommodate the tube 55 and obturator 51. This is shown in FIG. 14 wherein distal ends 54,64 of the obturator 51 and air tube 55 engage inner protrusions 50 on needle sections 13,14 separating ends 44 to the dotted line position.

Figure 15:
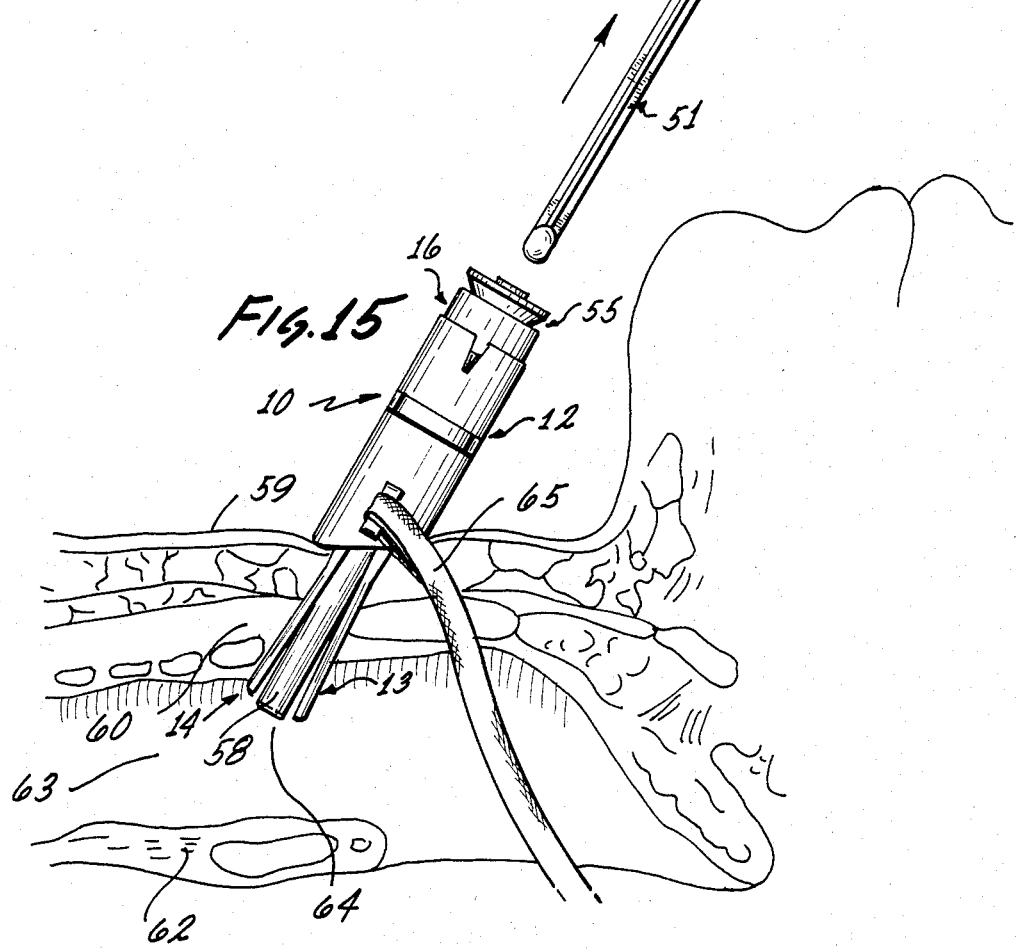

Referring now to FIG. 15, obturator 51 is removed and air tube 55 extends down into the airway of trachea 63 leaving a clear passage for air to reach the lungs. A small diameter air tube is inserted first to get air in fast which allows the patient's chest to expand and bring up any foreign object if that is what is causing the obstruction. The internal taper of needle sections 13,14 provided by protrusions 50 permits gradual expansion of ends 44 without danger of popping out of the incision in the membrane 60. In the prior art devices, the needle ends came to sharp points which points might push against posterior wall 62 and cut it. Also, when the tube end hits the reduced neck area of the prior art needle sections, it might open or part the sections too soon or push back (i.e., out of the trachea) the device.

As seen in FIGS. 6 and 7, the distal ends of needle sections 13,14 are tapered to blend into the sharp end of stylet 11 thereby allowing insertion without significant resistance. Be inserting the obturator and air tube together, tissues or blood are prevented from entering the air tube.

If desired, a smaller diameter air tube can be withdrawn from the housing section 12 and another of larger diameter quickly and easily inserted, as in FIG. 13, without withdrawal of section 12. There is no need to redefine the trachea area with other instrumentation since, with prior art devices that had to be removed, the skin might move.

The method disclosed herein conforms to standards of the National Academy of Science. Airway tubes of six millimeters in diameter are used for adults. The brackets 28,29 can be used to secure a tie 65 thereto (FIG. 15) by threading the same in brackets 28,29. A conventional universal adapter (not shown) may be connected to the top of housing section 12 with expansion of the lungs started by mouth-to-airway respiration with the operator's fingers closing off the passageway through housing section 12.

Figure 16:
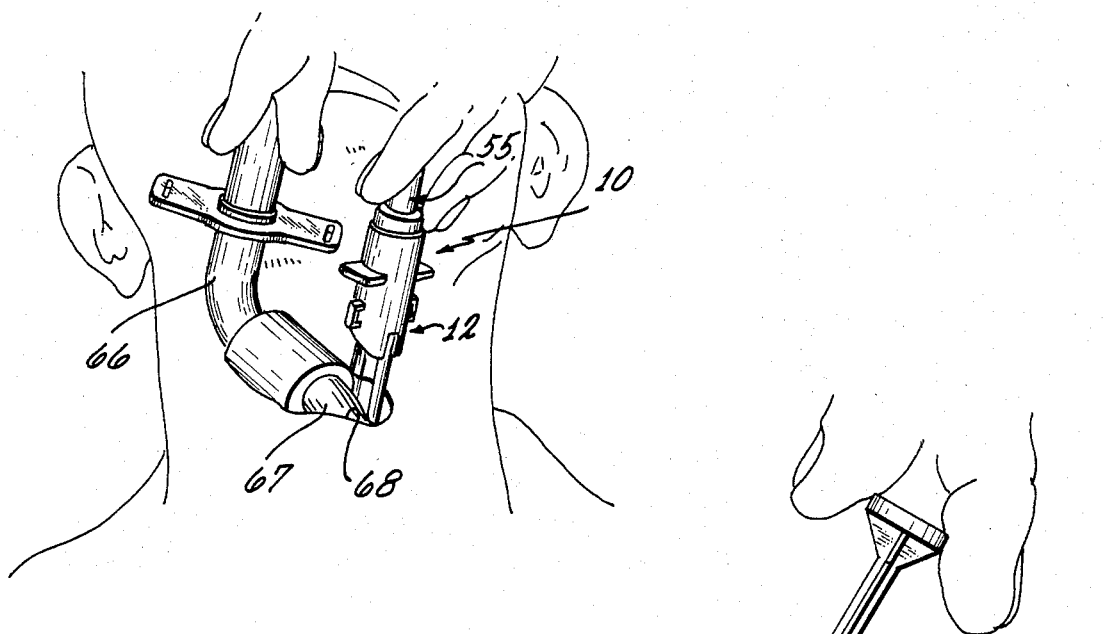
FIG. 16 is an illustration of an additional feature of the improved method of my invention.

The tracheotomy tube of a closed system may be quickly and easily connected to my invention. As shown in FIG. 16, airway tube 55 is first partially and slowly withdrawn thereby separating needle ends 44 allowing the patient to breathe through the housing section 12 which is inserted into opening 68 in the patient's neck. This expands opening 68. The plastic bag 67 at the end of tracheotomy tube 66 (coupled to a conventional closed system-not shown) is then inserted into the expanded opening 68 while the spread apart needle ends 44 are simultaneously withdrawn. This allows the operator to go to a closed system without the need for gouging and making a bigger opening. As can be seen, the same opening 68 is used. The bag 67 then expands against the inner wall of the trachea, as is known in the art, preventing any vomitous or aspiration of material into the patient's lungs which can cause pneumonia or death.

The indicia on housing section 12 indicates to the operator the proper orientation for insertion so it enters at a proper angle. As heretofore mentioned, air tubes of various diameters may be used, such as 4, 6 or 8 millimeters.

Although the invention has been described with respect to tracheotomies, it has obvious applications in any operation where it is desired to expand an opening to allow surgical procedures or other instrumentations, such as in thoracic, intraabdominal, intra articular, intra spinal and cranial and intra cervical operations.

The invention disclosed herein is easier to use and may thus be used by a relatively unskilled operator without danger of puncture of the posterior wall which is soft and made of muscle and might thus kill the patient. The use of selective airways provides the right airway for the right patient and air flow is quickly restored with bleeding minimized. Overpenetration, as known in the use of prior art devices, is lessened and an opening is provided for quick connection of a closed system.

In summary, the stylet has an arcurate distal end to facilitate passage through the tissues and the needle is divided lengthwise into two sections held by suitable resilient means, such as an elastic band, this thus accommodating airways of various sizes. The tubular housing rests on the cricoid cartilage and its lower end is slanted to approximate the desired entrance angle of the needle. Stabilizers such as flanges on the main housing section steady the device for one-hand operation while brackets on the sides can be used to hold ties to secure the device to the patient.

The flared cuff or cap on the air tube prevents over descent into the main housing section and aids in removal. The particular size airway to be used depends upon the estimated trachea size. The obturator acts as a plunger to facilitate introduction of the airway or air tube and prevents clogging caused by tissue particles. The gradual taper provided on the inner wall of the needle sections prevents popping out of the device and avoids overpenetration. The cap of the airway or air tube is designed for easy removal of the air tube from the main housing section.

It can be seen that I have described an improved apparatus and method for performing emergency cricothyrotomies and other surgical procedures with less danger to the patient, particularly when used by relatively unskilled operators.

I claim:

1. A surgical device adapted to puncture human skin for performing an emergency tracheostomy comprising: a housing, a hollow needle insertible in and retained in said housing and having a proximal end portion and a distal end portion of a reduced cross-sectional area, said distal end portion of said needle comprising at least two sections which, taken together, define a throughbore and terminate in a blunt distal end; spring means for holding said sections of said distal end portion of said needle together and to enable said sections of said distal end portion of said needle to be separable from each other and expand radially from the said reduced cross-sectional area of said distal end portion; a stylet of lesser cross-sectional area than said distal end portion and insertible in said throughbore through said needle without expansion of said sections, said stylet having a distal cutting end for limited projection beyond said blunt distal end of said needle for a cooperative insertion of the distal ends of the needle and stylet into a skin incision, and a wider main body portion on the proximal end thereof; first indexing means on the proximal end of the housing and cooperative second indexing means on the main body portion of said stylet; an airway tube movable through said needle, subsequent to removal of the stylet from the proximal end portion thereof to the distal end thereof, said airway tube being of larger cross-sectional area than the said cross-sectional area of said distal end portion of said needle whereby to expand radially said distal end portion of said needle from its normal cross-sectional area as said airway tube is moved through the distal end portion and distal end of said needle, said needle including guiding means for guiding said airway tube through said needle and camming said needle sections apart gradually and progressively before the tube reaches the skin level, said guiding means including an intermediate portion on each of the needle sections, each intermediate portion of said needle sections having an elongated tapered internal area between said proximal end portion and said distal end portion thereof, said internal tapered area being defined by elongated protrusions extending along said intermediate portion and extending interiorly thereof for guidance of said airway tube from the proximal end portion into the distal end portion such that, when said needle sections have their ends inserted into the trachea of a patient, said airway tube engages said guiding means and said guiding means cams said needle sections apart gradually and progressively before the airway tube reaches the skin level.

* * * * *